United States Patent [19]

Polimeni et al.

[11] 4,154,822

[45] May 15, 1979

[54] POLYSACCHARIDE FOR ENHANCEMENT OF CARDIAC OUTPUT

[75] Inventors: Philip I. Polimeni; Jafar Al-Sadir, both of Chicago; Anthony F. Cutilletta, Flossmoor, all of Ill.

[73] Assignee: The University of Chicago, Chicago, Ill.

[21] Appl. No.: 710,699

[22] Filed: Aug. 2, 1976

[51] Int. Cl.$^2$ .......................................... A61K 31/715
[52] U.S. Cl. ...................................... 424/180; 536/1; 536/4
[58] Field of Search ............................. 424/180; 536/1

[56] References Cited

U.S. PATENT DOCUMENTS

| | | | |
|---|---|---|---|
| 3,830,910 | 8/1974 | Homsy | 424/180 |
| 3,849,554 | 11/1974 | Winitz | 424/180 |
| 3,911,915 | 10/1975 | Seifter et al. | 424/180 |

OTHER PUBLICATIONS

Smith Thesis "The Subacute Toxicity of Intravenously Administered Okra Mucilage," Clemson U. Library, May, 1973.

Primary Examiner—Johnnie R. Brown
Attorney, Agent, or Firm—Merriam, Marshall & Bicknell

[57] ABSTRACT

Polysaccharide substances—essentially consisting of rhamnose, galactose and galacturonic acid and preferably derived by extraction and purification of okra plant materials—are administered to provide selective rheological and hemodynamic effects and specifically to enhance cardiac output without substantial increment in circulatory (plasma) volume or concurrent inotropic, chronctropic or vasoactive effects.

5 Claims, 4 Drawing Figures

POLYSACCHARIDE FOR ENHANCEMENT OF CARDIAC OUTPUT

BACKGROUND OF THE INVENTION

The present invention relates generally to therapeutic methods and materials useful in selectively providing desirable hemodynamic effects in animals, including humans. More specifically the invention relates to administration of fluids containing relatively small amounts of certain selected polysaccharide materials to the blood of a patient for the purpose of enhancing cardiac output without substantially increasing blood volume or generating inotropic, chronotropic or vasoactive effects.

The prior art is profuse with proposals of methods and materials for developing curative, ameliorative and prophylactic effects respecting circulatory system disorders of widely differing etiology. Clearly of interest with respect to the background of the present invention are the art's many proposals for restoring and/or enhancing cardiac output to healthy and failing hearts upon the occurrence of underperfusion of vital tissue as in traumatic and functional hypovolemia, syncope and cardiogenic shock. A separate body of information has been developed relating to ameliorative and/or prophylactic treatment of atherosclerotic disorders. Of particular interest to the background of the invention are prior proposals for treating and preventing atherosclerosis by administration of substances suspected of having beneficial rheological effects on circulatory fluids.

I. Treatment Of Tissue Underperfusion

Included among the proposals of the art for treating underperfusion of vital tissues are such standard procedures as administering sympathomimetic vasopressive agents to effect elevation of coronary perfusion pressure; administering inotropic agents to enhance myocardial contractility; administration of chronotropic agents to alter cardiac periodicity; and application of intra-aortic counterpulsation techniques. The advantages and disadvantages of such procedures have been explored in detail. See, e.g., Weiner, "Rational Therapeutic Approach to Cardiogenic Shock" in Cardiovascular Drug Therapy, K.L. Melmon, editor, F.A. Davis, Philadelphia, 1974, pp. 223–237.

Where there has been external loss of blood, plasma or extracellular fluid or internal sequestration of plasma in areas of inflammation, the standard treatment procedure has been rapid additive restoration of blood volume to "normal" levels. Plasma replacement fluids capable of effecting such restoration are well known and include water solutions of dextran, albumin, dextrose and other solutes with osmotic and oncotic pressures similar to that of plasma. Selection of solutions for use as plasma replacement fluids is made with great care. The choice of any particular solute is often complicated by the potential for increased capillary permeability to solutes (e.g., albumin) during hemorrhagic shock, the potential for exceeding tissue oncotic pressure and likelihood of interstitial pulmonary edema attendant administration of any noncolloidal fluids. While research on solutes has proceeded for many decades, very few solutions have received widespread clinical use.

Among the many proposals for plasma substitutes made in the last 25 years is that of Benjamin, et. al, Rev. Can. Biol., 10, 215–221 (1951) which discloses a saline solution including an alcohol-extracted okra plant mucilage. This "2% okra plasma" was reportedly administered to hemorrhaged dogs, in amounts equal to blood lost. The animals, while profoundly anemic and deficient in plasma proteins, were said to have experienced substantial restoration of blood pressure and circulatory volume—sufficient to maintain vital functions until restoration of lost blood components could be effected.

II. Drag Reducing Agents

Knowledge of the capacity of certain polymers to reduce turbulent flow of solvents in tubes has prompted various proposals that natural and synthetic polymeric agents be administered to animal circulatory systems to diminish turbulence suspected to exist in arterial flow. Proposals for administering polymeric "drag reducing" agents to blood have consistently emphasized that the additives would have clinical potential only in diminishing resistance to blood flow in those regions of the circulatory system where turbulence is likely to occur. Alternatively stated, the drag reducing potential of polymers is believed exclusively applicable to provide a benefit in large blood vessels and regions of arterial irregularity where velocity and vessel diameters would admit to turbulence. The additives are not expected to decrease resistance to flow in normal arteries wherein flow is laminar in character. [See, e.g., Stein et al., Medical Research Engineering, 11: 6–10 (1972); cf., Driels, et al, Nature, Vol. 259, No. 5542, pp. 389–90 (1976)]. Despite consistent authority to the effect that arterial blood flow is probably "disturbed" but not truly turbulent [see, e.g., Yellin, "Laminar-Turbulent Transition Process In Pulsatile Flow", Circulation Research, Vol. XIX, 791–804, 803 (1966)] suggestions for use of turbulence reducers in one form or another continue to be made.

U.S. Pat. No. 3,590,124 by Hoyt proposes the addition of 5–100 parts per million of high molecular weight water-soluble polyethylene oxides, polyacrylamides and linear polysaccharides to such blood transfusion fluids as dextran solutions, normal saline and liquid human plasma. The projected result of such practice is rather vaguely stated to be a reduction of turbulent friction within the transfusion fluid additive itself and a resultant reduction of body pumping requirements for the person receiving the transfusion. Polymers assertedly useful in such a manner are those exhibiting more or less classical drag reducing properties such as were catalogued by Hoyt in Polymer Letters, Vol. 9, pp. 851–862 (1971). Expectedly, the claimed advantages of the aforesaid patent were attributed to the use of those materials (such as selected high molecular weight polyethylene oxides) which commonly exert the most powerful influences on turbulent flow hydrodynamics in pipes, i.e., provide maximum drag reduction of water solutions at very small concentrations of 100 ppm or less.

Recent investigations into potential biomedical applications of polymeric drag reducing agents (see, e.g., Paper H2, Int'l Conf. on Drag Reduction, 1974, Cambridge, England, pages 17–27) provide reports of in vitro turbulence reduction by 40 ppm polyacrylamide additions to pooled blood samples. Other preliminary reports have dealt with the effect of drag reducing agents in decreasing turbulence in oscillatory flow; in diminishing destruction of red blood cells during extracorporeal circulation; and in lessening plaque accumulation in rabbit arterial tissue.

Presentations at the 1974 National Conference on Polymers and Lubrication at the University of Brest expressed interest in the idea of using drag reducing additives in the blood to treat cases of heart disease or arteriosclerosis. It was projected that if turbulence could be reduced in the circulatory system, there might be a reduction in required heart pumping power. Briefly alluded to as among the more promising polymers was a natural polysaccharide derived from okra plants—a substance which possesses marginal drag reducing properties in water solution (See, Hoyt, supra, at p. 858). This annotation of biomedical potential for plant extracts is consistent with an earlier publication [Castro, et al., "Reducing Fluid Friction With Okra," Chem. Tech. 1: 697–701 (1971)] which proposed that, at rather low concentrations, an aqueous solution of an okra plant mucilage might be useful in relieving turbulence in certain normal and pathologically altered portions of the circulatory system, though, again, not in vessels where flow is laminar. The latter publication is noteworthy for its cross reference to the plasma substitute work of Benjamin, et al., supra, wherein the general non-toxicity of "okra plasma" as a blood expander was advanced.

The above-described prior art of interest to the background of the present invention reveals no correlation between known methods and materials for treating tissue underperfusion through volume expansion, inotropic, chronotropic or vasoactive agents and proposals for reducing blood turbulence and required heart pumping power by administration of known drag reducing agents to the circulatory system. Such correlation is in fact belied by the findings of collateral studies on drag reducing agents as blood additives and on general rheological influences on cardiac output.

It is noteworthy that when effects of drag reducing agents on turbulent flow properties have been studied there recurs a consistent notation that, while flow through a partially occluded blood vessel may be preferentially increased by addition of a drag reducing agent, flow through healthy vessels is usually laminar and not affected by addition of polymers. See. e.g., Greene, et al,. Biorheology, Vol. 7, pp. 221–223 (1971). Significantly, it has also been noted that the apparent viscosities of blood (measured in vitro as a function of shear rate) to which small quantities of drag reducing agents were added either remained unchanged (Green, et al., supra) or increased (Stein, et al., supra).

Such reports on the lack of efficacy of drag reducing agents in diminishing flow resistance in "healthy" blood vessels and on possible increases in blood apparent viscosity upon addition of drag reducing agents indicate no promise of clinical potential for the polymers in treatment of tissue underperfusion disorders. This is especially the case upon consideration of studies of cardiac output which have demonstrated that cardiac output and venous return (key factors in the underperfusion problem) are essentially inversely proportional to blood viscosity. As noted above, blood viscosity appears likely to increase upon polymer addition. It has also been found than any changes in arterial resistance to blood flow (as might be obtained by adding polymers) have considerably less effect on venous return than corresponding changes in venular and venous resistance.

In sum, separate and distinct bodies of information have been developed concerning: (1) relieving tissue underperfusion by plasma expansion and inotropic, chronotropic and vasoactive drugs; and (2) reducing turbulence in blood vessels with natural and synthetic polymers as blood additives. There has been no recognition of overlapping clinical utility of preferred methods and materials with respect to the two fields of inquiry.

BRIEF DESCRIPTION

The present invention relates to the discovery that certain selected polymers possess enormous clinical potential as therapeutic agents in the treatment of tissue underperfusion. According to one aspect of the invention small quantities of purified polysaccharide material, essentially consisting of a rhamnose, galactose and galacturonic acid copolymer, are administered to an animal's circulatory system to provide significant increases in mean and peak cardiac output, stroke work, stroke power and flow acceleration without substantial increase in circulatory volume or substantial concurrent inotropic, chronotropic, or vasoactive effects.

Of substantial interest is the observation that while administration of the polysaccharide does not induce inotropic effects on the normal myocardial left ventricular pressure, the first derivative of left ventricular pressure (dP/dt), and aortic pressure, are enhanced in the failing heart, presumably due to increased coronary perfusion. The present invention therefore has expected utility and beneficial therapeutic effect with regard to a wide spectrum of cardiovascular diseases, many of which have a "high viscosity syndrome," [Dintenfass, Arch, Internal Medicine, 118 pp. 427–35 (1966)] and including: (1) the failing or weakened heart; (2) ischemic heart disease inclusive of myocardial infarction, angina pectoris, and some arrhythmias; (3) valvular or vascular constrictions, including atherosclerosis and certain types of geriatric senility; (4) hypertension caused by high peripheral resistance; (5) polycythemia; (6) sickle cell anemia; and (7) thrombus formation secondary to hemostasis.

Polysaccharide materials of the invention are preferably prepared through extraction and purification of okra or other plant tissue to provide a stable, non-toxic, powdered substance which dissolves easily in physiological saline, 1–10 mg or more per ml solutions are easily prepared. The preferred polysaccharides may be obtained in varying degrees of purity and are characterized by high molecular weight (on the order of $10^6$), substantial linearity and negative electrical charge at physiological pH conditions.

The remarkable benefical effects of practice of the invention cannot be accounted for in terms of reduction of arterial flow turbulence but rather appear to be related to alterations in blood flow characteristics throughout the vascular system and especially on the venous side. While not yet fully illucidated, the mechanism of action of the polysaccharides is believed to involve a generalized modification in the fluidicity of blood in vivo such that venous return, and thus cardiac output, is markedly enhanced. Support for this mechanism resides in the wholly unexpected finding that substantial reductions in apparent visocsity occur upon administration of the polysaccharide to blood, which reductions cannot be confirmed in plasma or water solutions of equivalent polysaccharide concentration.

The nature and scope of the present invention will be understood upon consideration of the following detailed description, reference being made to the drawing wherein.

Figure 1:
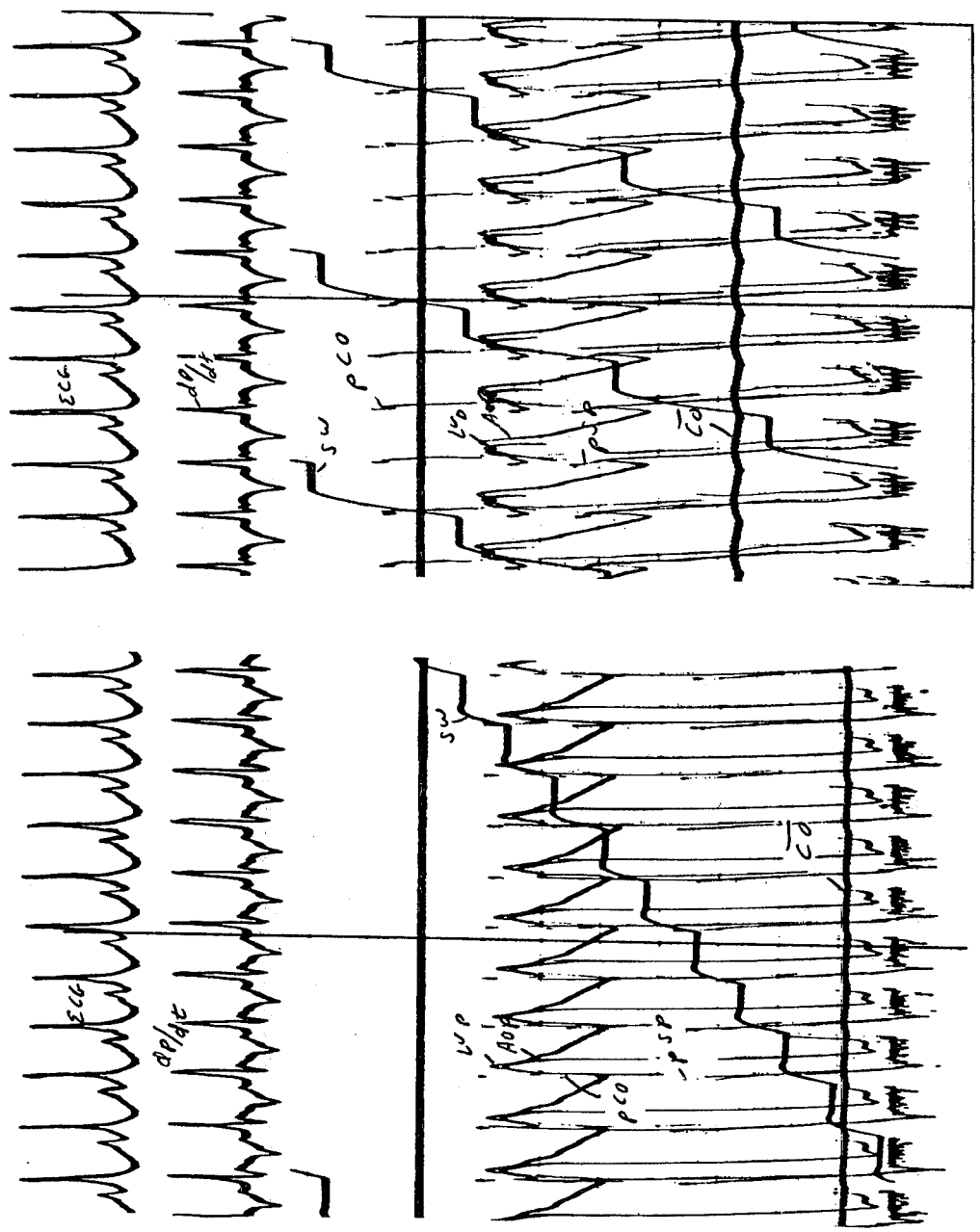
FIG. 1 is a composite graphic representation of cardiovascular functions measured before and after administration of materials of the invention to a healthy animal.

In subsequent description of practice of the invention, the following abbreviations may be employed:

| | |
|---|---|
| $Ao_p$ | aortic pressure (mmHg) |
| $\overline{Ao_p}$ | mean aortic pressure (mmHg) |
| $\overline{CO}$ | mean cardiac output (ml/min.) |
| pCO | peak cardiac output per beat (ml/min.) |
| dF/dt | flow acceleration (ml/sec.$^2$) |
| dP/dt | 1st derivative of pressure (mmHg/sec.) |
| HR | heart rate (beats/min.) |
| Imp. | aortic impedance at zero flow (mmHg/ml/sec.) |
| $LV_p$ | left ventricular pressure (mmHg) |
| R | resistance (mmHg/ml/min.) |
| pSP | peak stroke power per beat (gm-M/sec.) |
| $\overline{SP}$ | mean stroke power (gm-M/sec.) |
| SV | stroke volume (ml/beat) |
| SW | stroke work per beat (gm-M) |

DETAILED DESCRIPTION

The following Examples 1, 2 and 3 relate to preferred methods for preparation of polysaccharide materials of the invention from okra plant tissue.

EXAMPLE 1

A. Fresh okra is first homogenized in a Waring Blender and then filtered through cheesecloth to remove seeds and gross particulate matter. The filtrate is re-homogenized in a rotary blender for at least two minutes and, throughout the remaining preparation steps, kept in an ice bath where possible. The re-homogenized mixture is centrifuged at 15,000 rpm for two hours and the supernatant saved. To the supernatant is added and aqueous solution of $(NH_4)_2SO_4$ (0.42 gm/ml) and the mixture is stirred slowly in an ice bath for one hour. The material is then centrifuged at 15,000 rpm for 90 minutes to two hours. The pellet is retained and dissolved in excess 0.9% saline. The resulting solution is dialyzed against 0.9% saline for approximately 48 hours, using at least a 1-10 volume ratio and 3 changes in dialysis fluid. The dialyzed material is thereafter centrifuged at 90,000 g for one hour and the supernatant retained.

B. The following purification steps may be performed at ambient temperatures. One volume of 10% cetylpyridinium chloride (CPC) is added to 5 volumes of the above-prepared supernatant. While stirring a flocculent precipitate develops. The mixture is centrifuged at 2,000 rpm for 10 minutes. The precipitate is collected, washed once with water and dissolved in 2 M. sodium chloride/20% ethanol solution in a volume sufficient for solution of the precipitate. Two volumes of 95% ethanol are added and the precipitate is collected. The precipitate is re-dissolved in the saline/ethanol mixture, washed three times with 2 volumes of 95% ethanol and once with ethyl ether. The washed precipitate is dried in a dessicator overnight and dissolved, at a concentration of 1.0 mg per ml, in 0.9% saline.

EXAMPLE 2

A partially purified polysaccharide suitable for use in accordance with the invention may be prepared by practice of the procedures set out in part A of Example 1, i.e., without the CPC precipitation and subsequent washing steps—the supernatant of part A constituting the final product.

EXAMPLE 3

A crude polysaccharide suitable for use in accordance with the invention may be prepared by practice of the procedure of part A of Example 1 but eliminating the ammonium sulfate precipitation step and attendant centrifugation.

The above examples reveal that a suitable procedure for extraction of the okra polysaccharide would include the essential steps of homogenization, gross fluid fraction separation, dialysis of the fluid fraction and fine fluid fraction separation. Additional steps to enhance purity include an ammonium sulfate precipitation prior to dialysis and a CPC precipitation after dialysis.

Analysis of the okra polysaccharide copolymer of Example 1 reveals rhamnose, galactose and galacturonic acid constituents in the relative molar ratio of about 10:27:25. Chromatographic analysis reveals negative charges on the polysaccharide, likely due to the galacturonic acid constituent. The polysaccharide is retained on a molecular sieve designed to allow passage of globular molecules having a molecular weight less than about $10^6$.

EXAMPLE 4

Four functional types of rats having a body weight of about 0.25 kg. were tested with the material of Example 2: normal rats, spontaneously hypertensive rats, rats with a fixed obstruction to left ventricular outflow, and rats in low output shock. Each rat underwent instrumentation for hemodynamic study under general anesthesia. Following baseline recordings, small amounts (0.1 ml) were administered intravenously up to 1 or 2 ml. Recordings were taken with each injection. Throughout the studies, no adverse hematological effects were observed in the animals receiving the test substances.

Referring first to FIG. 1, the functions ECG, dP/dt, SW, SP, $LV_p$, $Ao_p$, pCO and $\overline{CO}$ are plotted for a typical normal animal before and after administration of 1 ml of the polysaccharide. Comparison of these functions reveals that although $LV_p$, $Ao_p$ and the dP/dt remain unaltered, SW, SP, $\overline{CO}$ and PCO are significantly enhanced.

Figure 2:
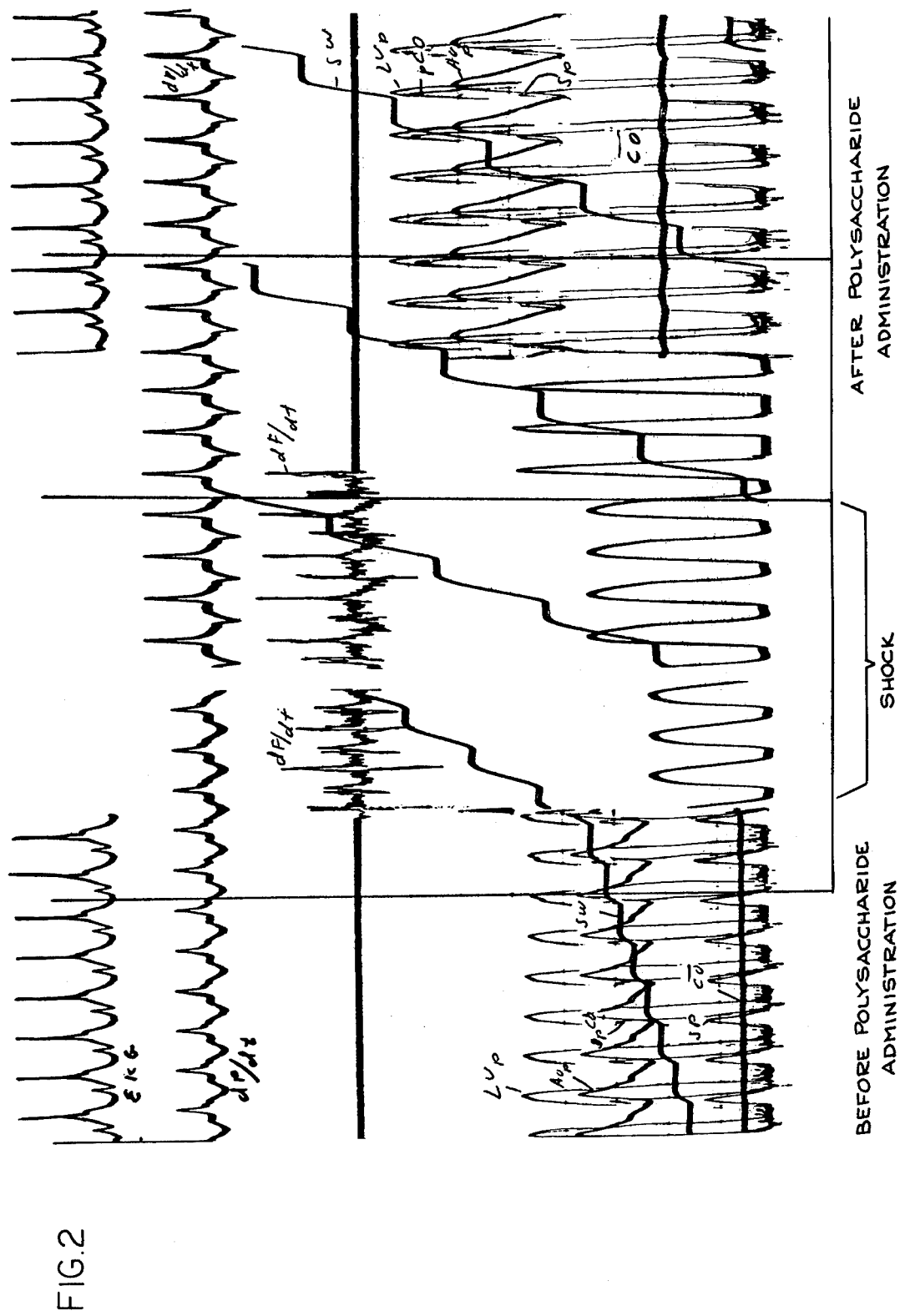
FIG. 2 is a composite graphic representation of cardiovascular functions measured before and after administration of materials of the present invention to an animal experiencing severe myocardial depression.

In FIG. 2, relating to identical cardiovascular functions for an animal in low output shock, there is additionally exhibited an enhanced dP/dt and a return of $LV_p$ and $Ao_p$ to normal, indicative of enhanced myocardial performance secondary to increased cardiac output and probably coronary blood flow.

Table 1 provides a composite illustration of relative effects of the practice of the invention as in Example 4, showing increases and decreases in certain circulatory functions upon administration of the polysaccharide to normal rats, rats with a fixed obstruction to left ventricular outflow (LV Banded) and rats with spontaneous hypertension (SHR). Also illustrated in Table 1 are relative effects of adminstration of 10 mg. of the potent vasodilator, phenoxybenzamine (an α-adrenergic blocking agent), to normal and spontaneously hypertensive rats.

In the table (as well as in Table 2) the following wholly subjective designations are employed: Relative stability of a particular function is designated by the symbol "0"; slight increases are designated "1"; substantial increases are designated "2"; extraordinary increases are designated "3"; and a decrease of any kind is designated "-1".

tion of left ventricular systole and its simultaneously computed first derivative using the mathematic function:

Vce=(LVdp/dt)/kDP in sec$^{-1}$ where:

DP=developed LV pressure; and k=series elastic constant.

Signals are recorded on an eight channel ink-recording system.

TABLE 1

| SUBSTANCE AND ANIMAL STATE | FUNCTION | | | | | | | | |
|---|---|---|---|---|---|---|---|---|---|
| | HR | LV$_p$ | dP/dt | $\overline{CO}$ | pCO | pSP | SW | dF/dt | Imp |
| Polysaccharide | | | | | | | | | |
| Normal rats | 0 | 0 | 0 | 3 | 2 | 2 | 2 | 2 | −1 |
| L.V. Banded rats | 0 | 1 | 0 | 3 | 2 | 2 | 2 | 1 | −1 |
| S.H.R. rats | 0 | 1 | 0 | 3 | 2 | 2 | 2 | 2 | −1 |
| Phenoxybenzamine | | | | | | | | | |
| Normal rats | 0 | −1 | 0 | 1 | 2 | 3 | 1 | 3 | * |
| S.H.R. | 0 | −1 | 0 | 0 | 1 | 0 | −1 | 1 | −1 |

*Not measured

Table 2 provides a composite illustration of relative effects of practice of the invention as in Example 4, showing increases and decreases in certain circulatory functions upon administration of the polysaccharide to normal rats to which the β-adrenergic blocking agent, propanolol, and the sympathomimetic drug, methoxanine, had previously been administered. These results indicate that the mode of action of the polysaccharide is neither an enhancement of the inotropic state of the myocardium nor vasodilotation at the peripheral vasculature.

TABLE 2

| SUBSTANCE | FUNCTION | | | | | | | |
|---|---|---|---|---|---|---|---|---|
| | HR | LV$_p$ | dP/dt | $\overline{CO}$ | pCO | pSP | SW | dF/dt |
| Propanolol | −1 | 1 | −1 | 0 | 1 | 1 | 0 | −1 |
| Polysaccharide | 0 | 0 | 0 | 2 | 2 | 2 | 2 | 2 |
| Methoxanine | 0 | 1 | 0 | 0 | −1 | 2 | 2 | 0 |
| Polysaccharide | 0 | 0 | 0 | 2 | 3 | 2 | 2 | 2 |

EXAMPLE 5

The following procedures are employed in studies of administration of the polysaccharide to dogs.

Mongrel dogs weighing 12-15 kg are used. The animals are anesthetized with an intravenous solution of alpha-chloralose and respiration is controlled by a Harvard volume respirator connected to a tracheotomy tube. Systemic arterial pressure is measured through a short 14-T gauge semirigid catheter and connected to a Statham P23 De pressure transducer. The heart is exposed by a mid-sternal thoracotomy; a pericardiotomy is performed and a pericardial cradle created to support the exposed heart. Left ventricular pressure is measured at the midpoint of the right atrium through a short 14-T gauge semirigid catheter inserted in the left ventricular apex and connected directly to a Statham P23 De pressure transducer without intervening tubing. An electromagnetic flow meter cuff probe is placed around the main pulmonary artery and blood flow is measured with a dual channel gated sine wave flowmeter (Biotronix Lab). The first derivatives of left ventricular pressure (LVdp/dt) and flow (df/dt) are computed electronically by operational amplifiers and resistance-capacitance differentiating circuits with a time constant of 0.5 msec and phase lag of less than 1 percent. Maximal velocity of left ventricular contractile element shortening (Vce) is assessed by analysis of the isovolumic por- Parameters are measured at control and during drug infusion by means of 10 cc boluses of polysaccharide preparation of Example 3 through a catheter in the femoral vein.

To date, dog experiments conducted according to the procedures of Example 5 have provided dramatic, though somewhat inconsistent, results. The initial responses to intravenous injection of a crude polysaccharide (prepared according to Example 3) were variable, presumably due to variations in concentration of the polysaccharide and the presence of impurities in the injection fluid. At Ao$_p$ systolic levels of 80 mmHg or less, the polysaccharide caused variable increases in pulmonary arterial flow up to 288% and a widened Ao$_p$ impulse with no increase in HR or dp/dt. LV$_p$ was either unchanged or slightly decreased. These results suggest that the pulmonary artery flow increment is not due to an inotropic or chronotropic effect. The size of the increment, together with the simultaneous elevation of Ao$_p$ observed in some experiments, also make it unlikely that the flow increment can be explained by vasodilation. Among the many experimental animals treated, two dogs exhibited what appeared to be anaphylactic shock after adminstration of the crude preparation and expired.

EXAMPLE 6

Figure 3:
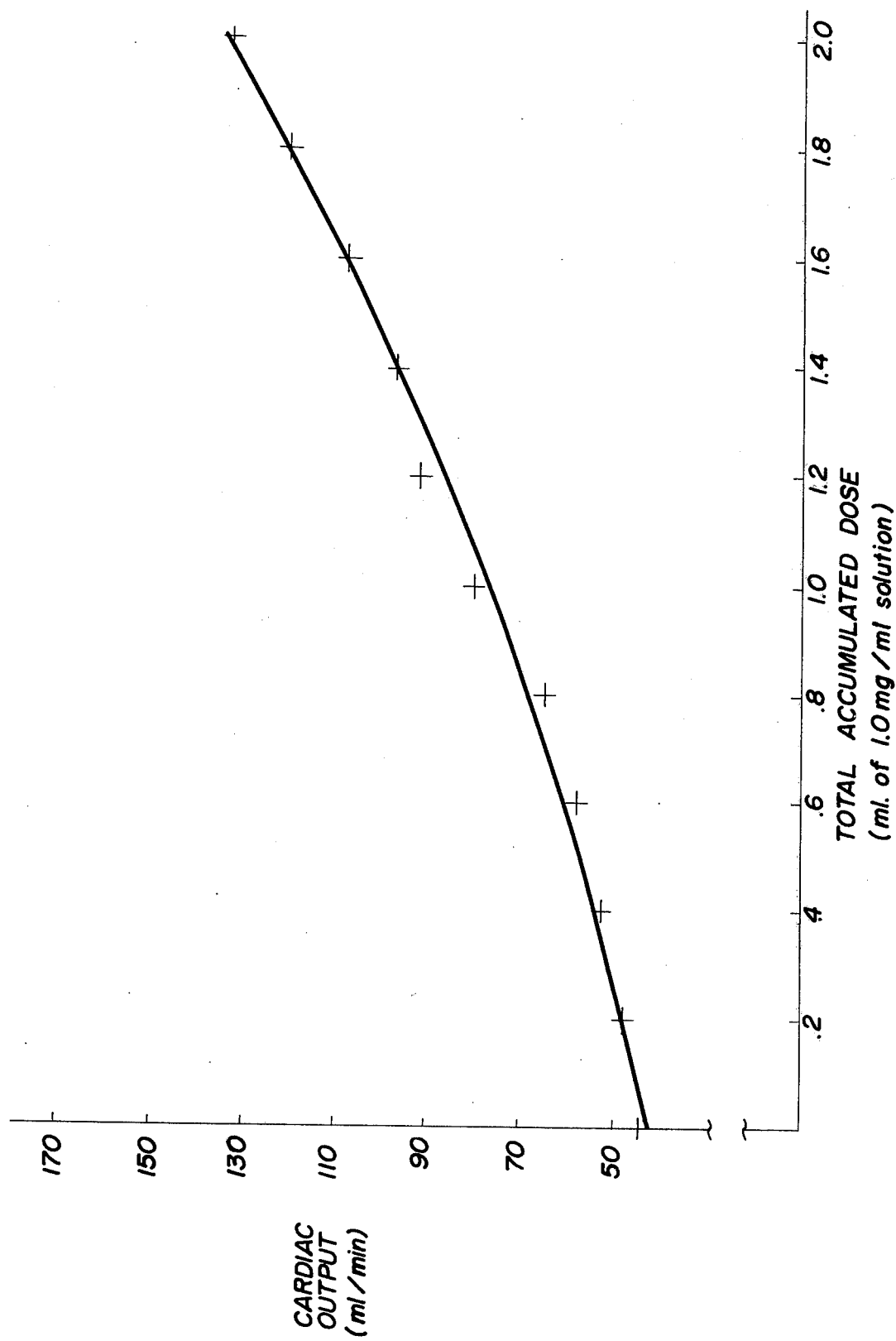
FIG. 3 is a graphic repesentation of dose dependent response of cardiac output to administration of polysaccharides of the invention

A typical dose response curve correlating the increase in a mean cardiac output in the rat to increasing dosages of purified polysaccharide prepared according to Example 1 is illustrated in FIG. 3. The 1.0 mg/ml polysaccharide solution was administered intravenously to five rats weighing about 0.25 kg in 0.2 ml aliquots and the increment in mean cardiac output measured. After administration of 5 mg/kg, mean cardiac output had increased by at least 75%.

EXAMPLE 7

Figure 4:
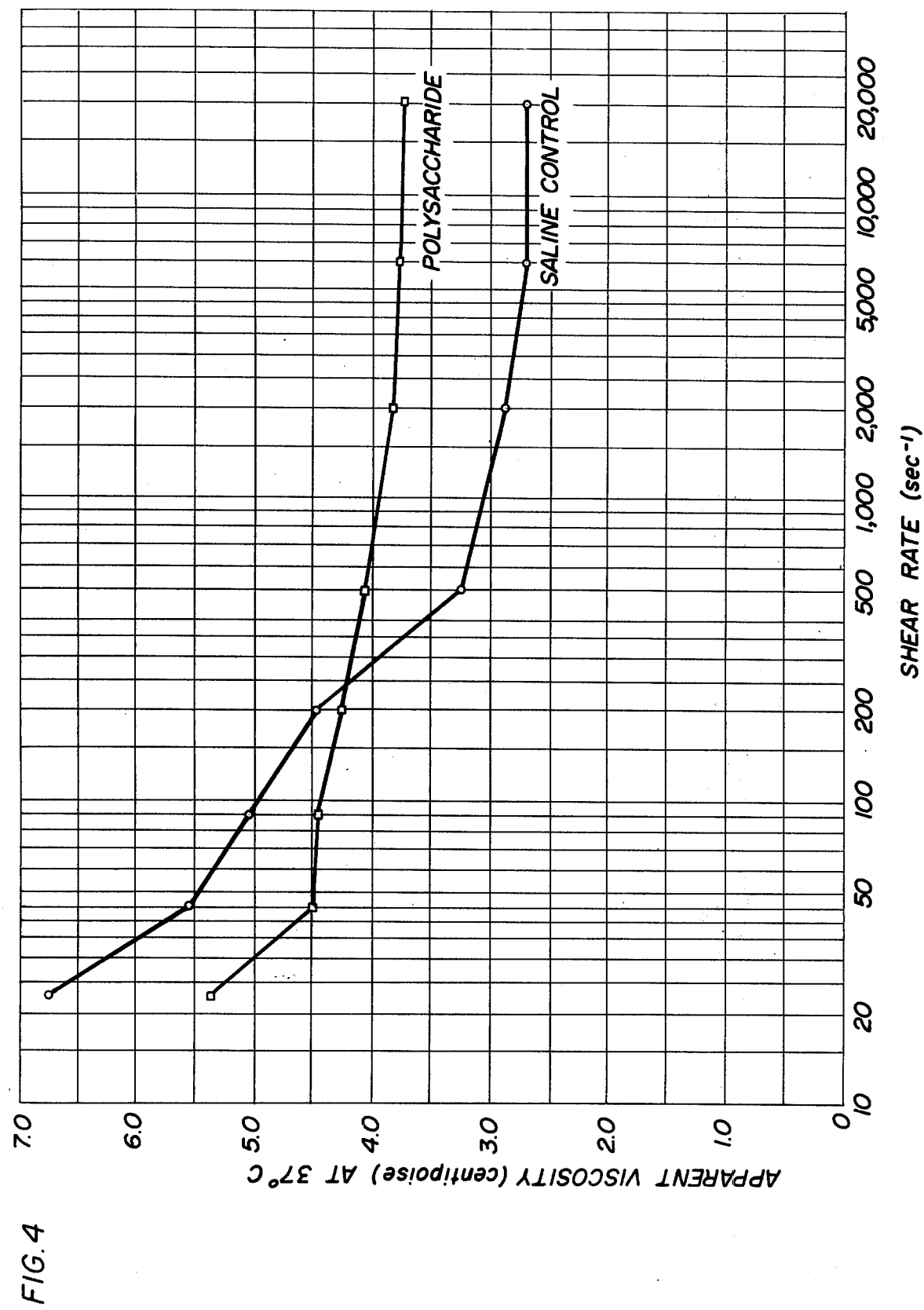
FIG. 4 is a graphic representation of blood apparent viscosity (as a function of shear rate) with and without addition of polysaccharides of the invention.

FIG. 4 illustrates the results of analyses of apparent blood viscosity as a function of shear rate upon addition of dosage amounts of polysaccharide material to rat blood. Rats weighing approximately 0.25 kg were injected intravenously with a 1 mg. dose of the polysaccharide solution prepared according to Example 1. Shortly after administration blood was withdrawn from the inferior vena cava of experimental and control animals. Analyses were performed on a Brookfield microviscosimeter and Weissenberg rheogomiometer over shear rate ranges of 20–200 sec$^{-1}$ and 500–20,000 sec$^{-1}$, respectively. The former ranges represent those commonly believed to be encountered in an animal vascular system. Some blood rheologists believe that ranges of shear rates approaching zero are important in vivo. Starting at the lowest shear rates measured, the apparent viscosity of blood from control rats fell rapidly from 7 cP to slightly under 3cP. The apparent viscosity of blood from rats administered the polysaccharide fell from an initial value of slightly more than 5 cP. to slightly under 4 cP. Furthermore, control blood became quasi-Newtonian at shear rates in excess of about 500 sec$^{-1}$ while the experimental blood became quasi-Newtonian at a shear rate under 50 sec$^{-1}$. It is expected that at in vivo shear rates of from about 0 to about 200 sec$^{-1}$, substantial decreases in the viscosity of blood will occur upon addition of from about 1 to 100 mg/1 of polysaccharide.

It is proposed that the mechanism of action of the polysaccharide additives of the invention as cardiac output enhancers involves the unexpected diminution of blood viscosity by the polysaccharide additive. This is believed to be the first demonstration of such a phenomenon—inconsistent as it is with reported increases in blood viscosity upon addition of drag reducing agents such as polyethylene oxide. Because no similar effects have been obtained when the polysaccharide is added to water or plasma, it is speculated that the viscosity drop in blood is the result of erythrocytes becoming aligned among extended, electrically charged polysaccharide macromolecules. It is not difficult to envision various modes of operation of the polysaccharide in vivo. The molecules may, for example, increase axial flow in small vessels merely by being repelled from the negatively charged walls of the vessel or by interacting with positively charged fibrinogen molecules to diminish clumping of erythrocytes. According to these models, the relative linearity of the rhamnose, galactose and galacturonic acid polysaccharide macromolecule, its high molecular weight and its uniform negative electrical charge all contribute in some measure to cause unusually beneficial hemodynamic effects.

The absolute significance of each of the characteristics of linearity, high molecular weight and electrical charge has not been fully delineated but the relative significance of the characteristics in selection of a polysaccharide for practice of the invention is manifest. Apart from standard considerations of toxicity, ease of synthesis or purification and the like, it is not expected that low molecular weight, substantially branched and electrically neutral polysaccharides or other polymers will provide the benefits of the present invention. For example, preliminary screening of several naturally-occurring polymers, including guar, karaya and locust bean gums as well as DNA, reveals no enhancement of cardiac output.

In the above description of preferred modes of administration, reference is made to solutions of polysaccharide in physiological saline. Clearly, numerous other aqueous carrier or solvent systems may be employed without departing from the spirit of the invention. Thus, for example, the polymer may likely be administered in solution with plasma without diminishing the desired result of increasing cardiac output by factors in excess of those which may incidentally result from concurrent expansion of plasma volume and hemodilution.

The clearly preferred mode of providing the polysaccharide to the circulatory system is intravenous, including infusion and injection. The amounts of polysaccharide to be administered to a particular patient may be subject to variation depending upon such factors as body weight and the etiology and extent of tissue underperfusion (i.e., whether the patient treated is encountering cardiogenic shock, ischemia, or the like). It is contemplated that further developmental studies performed in a manner consistent with the above illustrative examples will reveal preferred dosage ranges generally in keeping with the finding that substantial enhancement of cardiac output in rats is provided by a 5 mg/kg dose of purified okra plant polysaccharide of Example 1.

On the basis of percent investigation it is expected that aqueous solutions of from about 1 to about 20 and perhaps as much as 100 or more milligrams of polysaccharide may be administered per kilogram of the patient's body weight and that such administration may be repeated from one to five times per day.

Numerous modifications and variations of our invention are expected to occur to those skilled in the art upon consideration of the above description. It is expected, for example, that decreases in blood viscosity attendant to administration of polysaccharide according to the invention may prove to be most beneficial in extracorporeal circulation of blood. Consequently only such limitations as appear in the appended claims should be placed thereon.

What is claimed is:

1. In the method for developing therapeutrically beneficial hemodynamic effects through administering polymers to the blood of patients, the improvement comprising enhancing the cardiac output of a patient in need of such enhancement and independently of volume expanding effect by administering a linear, high molecular weight, negatively-charged polysaccharide essentially consisting of rhamnose, galactose and galacturonic acid.

2. The method of claim 1 wherein the amount administered is from about 1 to about 100 milligrams of polysaccharide per kilogram of the patient's body weight.

3. A fluid for introduction into the circulatory system of a patient to increase cardiac output without substantial concurrent increse in circulatory volume, said fluid comprising an aqueous solution of from about 1 to about 100 mg/ml of a linear, high molecular weight, negatively charged polysaccharide consisting of rhamnose, galactose and galacturonic acid constituents in a relative ratio of about 10:27:25, respectively.

4. A fluid according to claim 3 wherein said aqueous solution further includes 0.85% by weight sodium chloride.

5. A fluid according to claim 3 wherein said polysaccharide is an extracted constituent of okra plant tissue.

* * * * *